US00PP37143P3

(12) United States Plant Patent
Boynton-Steele

(10) Patent No.: US PP37,143 P3
(45) Date of Patent: Dec. 9, 2025

(54) ***SALVIA* PLANT NAMED 'DH002'**

(50) Latin Name: *Salvia hybrida*
Varietal Denomination: DH002

(71) Applicant: Desert Honed LLC, Boise, ID (US)

(72) Inventor: Nicholas A. Boynton-Steele, Boise, ID (US)

(73) Assignee: Desert Honed LLC, Boise, ID (US)

( * ) Notice: Subject to any disclaimer, the term of this patent is extended or adjusted under 35 U.S.C. 154(b) by 0 days.

(21) Appl. No.: 19/037,198

(22) Filed: Jan. 25, 2025

(65) Prior Publication Data

US 2025/0248321 P1 Jul. 31, 2025

Related U.S. Application Data

(60) Provisional application No. 63/627,192, filed on Jan. 31, 2024.

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ... A01H 5/02; A01H 5/00; A01H 5/12; A01H 6/508; A01H 6/50
See application file for complete search history.

*Primary Examiner* — June Hwu

(74) *Attorney, Agent, or Firm* — Weatherly IP Solutions, LLC; James Weatherly; Karen Bechtold

(57) ABSTRACT

A new *Salvia* plant designated 'DH002' particularly distinguished by greyed-green leaves with strong pubescence and a shrub height of 70 cm, is disclosed.

1 Drawing Sheet

CROSS REFERENCE TO RELATED MATTER

The present application claims priority to U.S. Application No. 63/627,192, as filed on Jan. 31, 2024, the entire contents of which is incorporated herein by reference for all purposes.

Genus and species: *Salvia hybrida.*

Variety denomination: 'DH002'.

BACKGROUND OF THE NEW PLANT

The present invention comprises a new and distinct variety of *Salvia*, botanically known as *Salvia hybrida*, and hereinafter referred to by the variety name 'DH002'. 'DH002' originated from a cross of the proprietary female *Salvia* plant '1603-5-T2' (unpatented) and the proprietary male *Salvia* plant '1200-6-P1'in June 2019 in Tucson, Arizona.

In fall of 2018 seeds were planted and a plant named 'DH002' was identified in the summer of 2019. 'DH002' was first vegetatively propagated by vegetative cuttings in Boise, Idaho. 'DH002' was found to reproduce true to type in successive generations of asexual propagation in Boise, Idaho via vegetative cuttings.

SUMMARY OF 'DH002'

The following are the most outstanding and distinguishing characteristics of 'DH002' when grown under normal horticultural practices in Boise, Idaho.

1. Greyed-green leaves with strong pubescence; and
2. Shrub height of 70 cm.

DESCRIPTION OF THE PHOTOGRAPHS

These new *Salvia* plants are illustrated by the accompanying photographs of plants grown in a greenhouse in Boise, Idaho. The colors shown are as true as can be reasonably obtained by conventional photographic procedures.

DESCRIPTION OF 'DH002'

Figure 1:
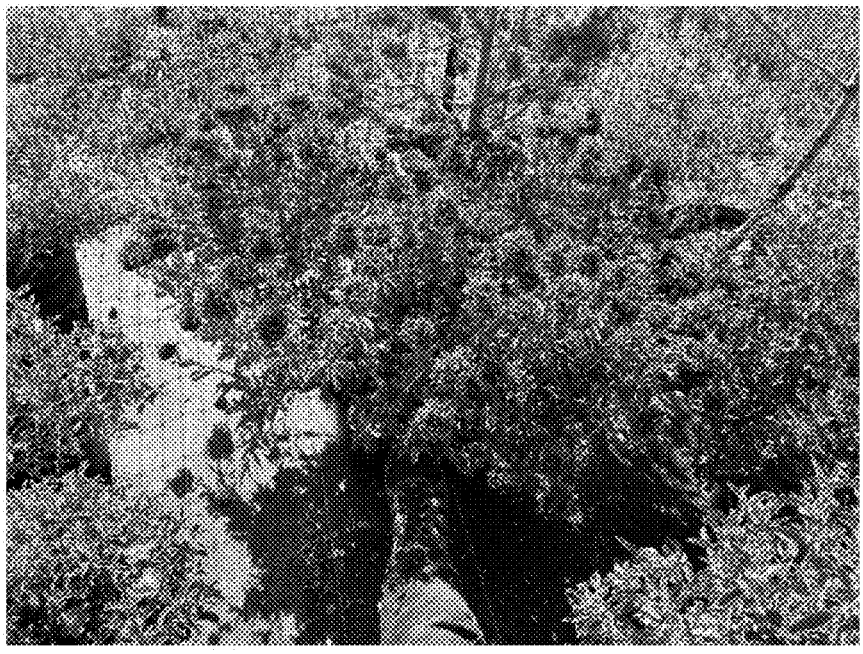
FIG. 1 is a whole plant photo of 'DH002' showing foliage, buds, and flowers. The photo is of a 2-year-old plant taken in June 2021 in Boise, Idaho.
Figure 2:
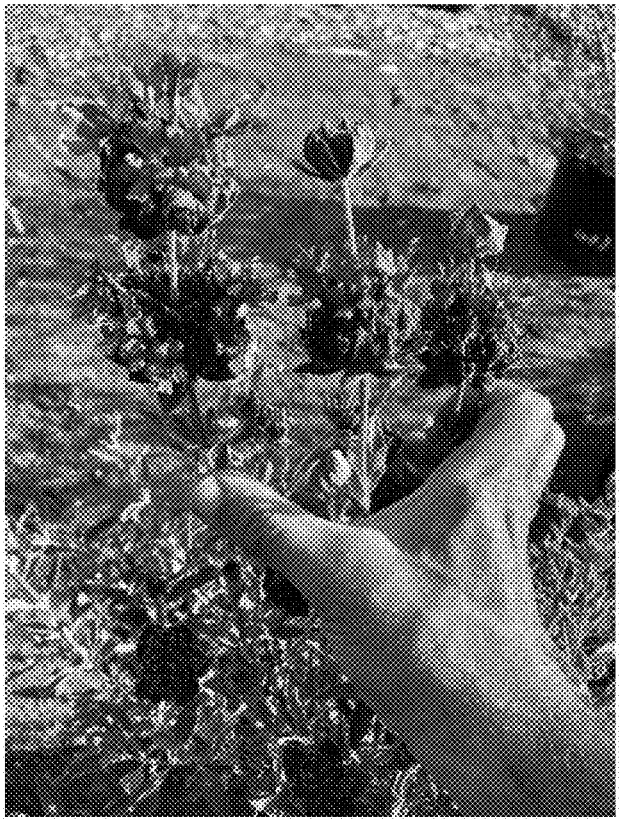
FIG. 2 is close-up photo of 'DH002' showing foliage, buds, and flowers. The photo is of a 1-year-old plant taken in June 2020 in Boise, Idaho.

The following detailed descriptions set forth the distinctive characteristics of 'DH002'. The data which define these characteristics were collected from asexual reproductions carried out in Boise, Idaho. Data was collected in January 2024 on one year old plants from cuttings in 3 gallon containers grown in a plastic greenhouse. Color references are to The R.H.S. Colour Chart of The Royal Horticultural Society of London (R.H.S.), 4$^{th}$ edition (2001).

Classification:

*Family.*—Lamiaceae.
*Genus.*—*Salvia.*
*Species.*—*Hybrida.*
*Common name.*—Sage.

Parents:

*Female.*—*Salvia* plant '1603-5-T2' (unpatented).
*Male.*—*Salvia* plant '1200-6-P1' (unpatented).

Plant:

*Propagation method.*—Cutting.
*Rooting system.*—Fibrous.
*Vigor.*—Medium.
*Time to develop roots.*—2 to 3 weeks.
*Crop time.*—2 months to finish a one gallon, 3 to 4 months to finish a 3 gallon.

*Suggested container size*.—One, three or five gallon containers.
*Use*.—Home gardens, commercial landscapes, native gardens, waterwise gardens, pollinator gardens.
*Type*.—Perennial.
*Overall dimensions*.—70 cm tall×100 cm wide.
*Cultural requirements*.—In ground, full to partial sun, infrequent deep watering, light shearing after main bloom season will keep the shrub compact.
*In containers*.—Full sun, well drained media, consistently moist, pinched in plug stage, pinched at least once more for a one gallon, at least twice more for a 3 or 5 gallon.
*Hardiness*.—USDA zone 8a.
*Form*.—Low, rounded shrub.
*Growth habit*.—Compact, rounded.
*Blooming season*.—Late spring through summer.
*Lastingness of blooms*.—Each flower 2 days, each inflorescence 4 to 6 weeks. Dried glomerules last for months.

Stems (below first pinch):
*Condition*.—Semi-ripe wood.
*Bark*.—Lightly tomentose becoming rough.
*Shape*.—Square in cross section becoming round.
*Length*.—6 cm to 8 cm.
*Diameter*.—0.3 cm.
*Bark color*.—RHS 165A and RHS 166C.
*Stem color* (*where exposed beneath bark*).—RHS 193A.
*Shape*.—Square in cross section becoming round.
*Texture*.—Lightly tomentose becoming rough.

Branches:
*Quantity*.—30 to 50.
*Shape*.—Square in cross section.
*Length*.—8 cm to 12 cm.
*Width*.—0.15 cm to 0.2 cm.
*Internode length*.—3.8 cm to 0.2 cm. Spring growth has larger leaves and longer internode lengths.
*Color*.—RHS 187A at branch tips, RHS 194B in middle, then fading to RHS 165A at base.
*Anthocyanin*.—Absent.

Leaves:
*Type, arrangement*.—Opposite.
*Attachment*.—Petiolate.
*Quantity per branch*.—8 to 16.
*Shape*.—Ovate to elliptical.
*Length* (*mature*).—3.0 cm to 5.3 cm.
*Width* (*mature*).—1.2 cm to 1.8 cm.
*Margin*.—Shallow crenate.
*Thickness*.—0.05 cm.
*Surface* (*adaxial*).—Strongly rugose, strongly pubescent.
*Surface* (*abaxial*).—Strongly pubescent.
*Color* (*adaxial surface*).—RHS 189A.
*Color* (*abaxial surface*).—RHS 191B.
*Venation*.—Pinnate in pattern, recessed from upper surface, protruding from lower surface.
*Vein color*.—RHS 194B.
*Apex*.—Acute to rounded.
*Base*.—Moderately taped to petiole.
*Fragrance*.—Musk, slight cineole.
*Stipules*.—Absent.

Petiole:
*Shape*.—D-shaped in cross section.
*Length*.—1.0 cm to 1.4 cm.
*Width*.—0.1 cm.
*Texture*.—Tomentose.
*Color*.—RHS 194C.

Peduncle:
*Length* (*from uppermost leaf pair to base of lowest whorl of flowers*).—5.5 cm to 6.5 cm.
*Shape*.—Square in cross section.
*Width*.—0.2 cm.
*Texture*.—Lightly tomentose.
*Color*.—RHS 194B with tones of RHS N77B.

Inflorescence:
*Type*.—One to three verticillasters, usually two.
*Flower arrangement*.—Opposite sessile cymes.
*Length*.—4 cm to approximately 12 cm depending on the number of verticillasters.
*Width*.—5.0 cm to 6.0 cm.
*Internode length*.—Approximately 3.5 cm between glomerules.
*Number of floret whorls or glomerules per flowering stem*.—Approximately 1 to 3.
*Number of florets per node*.—Approximately 35.

Bracts:
*Quantity*.—Approximately 28 to approximately 35.
*Length*.—2.0 cm to 2.2 cm.
*Width* (*at the widest point*).—0.6 cm to 1.4 cm.
*Shape*.—Linear, for the smallest bracts to ovate for the largest bracts.
*Apex*.—Acute.
*Base*.—Tapered, sessile, and from 0.1 cm to 0.4 cm wide at attachment to peduncle.
*Margin*.—Entire.
*Texture*.—Adaxial surface: Rugose, lightly tomentose. Abaxial surface: Rugose, moderately tomentose.
*Color*.—RHS 194B at the base to RHS N77A at the apex.

Calyx:
*Shape*.—Tubular.
*Length*.—2.1 cm.
*Width at base*.—0.2 cm.
*Sepal apices*.—Acute.

Sepals:
*Quantity*.—Fused into a calyx tube.
*Sepal length*.—3 lobes at end of tube; one adaxial surface: 0.7 cm; two abaxial surfaces: 0.2 cm.
*Sepal width*.—Adaxial surface: 0.7 cm; abaxial surface: 0.1 cm to 0.2 cm.
*Shape*.—Adaxial lobe flares out at end of calyx tube and then tapers to an acute apex, the adaxial lobes are narrow and taper to an acuminate apex.
*Apex*.—Adaxial acute, abaxial acuminate.
*Base*.—Fused into a tube.
*Margin*.—Entire.
*Texture*.—Exterior surface: Slightly rugose, lightly tomentose. Interior surface: Slightly reticulately-veined, smooth.
*Color* (*both surfaces*).—RHS 194B at base and RHS N77A at apex.

Flowers:
*Quantity*.—Approximately 35 per whorl.
*Aspect*.—30 to 60 degrees in relation to peduncle.
*Shape*.—Tubular, opening to a bi-radially symmetric flower.
*Blooming period*.—Early through late summer.
*Persistence*.—Individual flowers last approximately two days, individual inflorescences last 4 to 6 weeks.
*Fragrance*.—None.

Bud:

*Shape*.—Tube shaped with a rounded end.

*Dimensions* (*immediately before petal emergence*).—Length: 1.0 cm to 1.5 cm. Diameter: 0.2 cm to 0.3 cm.

*Color*.—RHS 93B at tip fading to RHS 92B at base.

*Surface*.—Smooth.

Corolla:

*Shape*.—Tubular, opening to a bi-radially symmetric flower with 5 petals.

*Length*.—2.6 cm.

*Width*.—0.5 cm.

*Color*.—RHS 93B fading to RHS 92D at base.

*Upper lip*.—Length: 0.6 cm. Width: 0.5 cm. Intensity of pubescence of outer side: smooth. Color: RHS 93B at petal margin, fading to RHS 93D in the body of the petal.

*Lower lip*.—Degree of undulation of margin: weak, 3 rounded undulations per lobe. Surface texture: smooth. Color: RHS 93B at petal margin, fading to RHS 93D in the body of the petal.

Petals:

*Quantity*.—5.

*Arrangement*.—Bi-radially symmetric.

*Upper petal*.—Shape: Elliptic to obovate. Length: 0.06 cm. Width: 0.05 cm. Texture: Adaxial surface: Smooth. Abaxial surface: Smooth. Apex: Rounded. Base: Fused to corolla tube, 0.4 cm wide at petal attachment to tube. Margin: Entire. Color (both surface): RHS 93B at petal margin fading to RHS 93D in the body of the petal.

*Side petal*.—Quantity: 2. Shape: Ovate to elliptic. Length: 0.6 cm. Width: 0.2 cm to 0.3 cm at attachment to tube, 0.5 cm at widest point. Texture (both surfaces): Smooth. Apex: Rounded. Base: Attached to corolla tube. Color (both surfaces): RHS 93B at petal margin, fading to RHS 93D in the body of the petal.

*Lower petal, lateral lobes*.—Shape: Narrow, fused, widening toward apex into two shallow lobes. Length: 0.8 cm to 0.9 cm in total, lobes 0.1 cm to 0.2 cm. Width: 0.04 cm. Texture (both surfaces): Smooth. Apex: Rounded. Base: Attached to corolla tube. Margin: Entire. Color (both surfaces): RHS 93B at petal margin, fading to RHS 93D in the body of the petal.

Reproductive organs:

*Stamens*.—Quantity: 2. Filaments: Length: 1.0 cm from corolla tube attachment to anther, fused to corolla tube, becoming free where tube flares. Color: RHS 93B.

*Anthers*.—Attachment, shape: Basifixed. Width: 0.2 cm. Color: RHS 14B.

*Pollen*.—Amount: Medium. Color: RHS 14B.

*Pistil*.—Quantity: 1.

*Style*.—Length: 3.2 cm. Diameter: 0.05 cm. Color: RHS 93B at tip fading to RHS 92D at the base.

*Stigma*.—Shape: Forked. Length: 0.2 cm. Diameter: 0.02 cm.

*Ovary*.—Shape: Cylindrical. Length: 1.0 cm. Diameter: 1.0 cm. Color: RHS 142B.

Seed:

*Quantity*.—2.

*Shape*.—Flattened oval.

*Length*.—0.3 cm.

*Diameter*.—0.1 cm to 0.15 cm.

*Surface*.—Smooth, shiny.

*Color*.—RHS N199C with darker vein-like markings of RHS N199B.

Disease and pest susceptibility: Occasional Powdery Mildew. Occasional *Pythium* or other water mold susceptibility in water-logged or poorly drained soil. Occasional aphid infestation in early spring on new growth.

COMPARISON OF 'DH002' WITH PARENTAL LINES AND KNOWN VARIETY

'DH002' is distinguished from the female parent as described in Table 1 and the male parent in Table 2.

TABLE 1

Comparison with Female Parental Line

| Trait | Variety 'DH002' | Female parent '1603-5-T2' |
|---|---|---|
| Leaf pubescence | Strong Pubescence | Foliage lacks pubescence |

TABLE 2

Comparison with Male Parental Line

| Trait | Variety 'DH002' | Male Parent '1200-6-P1' |
|---|---|---|
| Adaxial Leaf color | RHS 189A | RHS 190A with indumentum and RHS 191A under indumentum. |

'DH002' can be compared to the commercial *Salvia* variety 'Allen Chickering' (unpatented). Differences between the varieties are described in Table 3.

TABLE 3

Comparison with Similar Variety

| Trait | Variety 'DH002' | Commercial line 'Allen Chickering' |
|---|---|---|
| Height | 70 cm | 130 cm to 160 cm |

I claim:

1. A new and distinct variety of *Salvia* plant named 'DH002' as shown and described herein.

* * * * *